United States Patent [19]

Sjogren

[11] Patent Number: 4,732,762

[45] Date of Patent: Mar. 22, 1988

[54] TIMED RELEASE PEST CONTROL COMPOSITION AND MEANS

[75] Inventor: Robert D. Sjogren, St. Paul, Minn.

[73] Assignee: Metropolitan Mosquito Control District, St. Paul, Minn.

[21] Appl. No.: 714,341

[22] Filed: Mar. 20, 1985

Related U.S. Application Data

[63] Continuation of Ser. No. 472,922, Mar. 7, 1983, abandoned.

[51] Int. Cl.$^4$ .............................................. A01N 25/34
[52] U.S. Cl. ...................................... 424/409; 71/67; 71/DIG. 5; 424/408; 514/722
[58] Field of Search .............. 71/67, DIG. 5; 424/16, 424/19, 22, 23, 409, 408; 514/722

[56] References Cited

U.S. PATENT DOCUMENTS

| | | | |
|---|---|---|---|
| Re. 27,238 | 11/1971 | Stansbury et al. | 71/27 |
| 2,404,698 | 7/1946 | Dreyling | 167/30 |
| 3,264,184 | 8/1966 | Geiger et al. | 71/DIG. 5 |
| 3,576,760 | 4/1971 | Gould et al. | 252/403 |
| 3,882,226 | 5/1975 | Bradburne | 424/19 |
| 3,891,759 | 6/1975 | Aries | 424/219 |
| 3,904,662 | 9/1975 | Henrick et al. | 260/410 |
| 3,921,815 | 10/1975 | Henrick et al. | 424/312 |
| 3,950,181 | 4/1976 | Pilgrim | 106/306 |
| 3,953,378 | 4/1976 | Lasser | 852/522 |
| 4,023,955 | 5/1977 | Mueller | 71/64 F |
| 4,056,610 | 11/1977 | Barber, Jr. et al. | 424/32 |
| 4,082,533 | 4/1978 | Wittenbrook | 71/28 |
| 4,163,674 | 8/1979 | Been | 106/15.05 |
| 4,225,693 | 9/1980 | McCormick | 526/261 |
| 4,272,398 | 6/1981 | Jaffe | 252/316 |

FOREIGN PATENT DOCUMENTS

| | | |
|---|---|---|
| 1047272 | 1/1979 | Canada . |
| 2021259 | 11/1971 | Fed. Rep. of Germany . |
| 2743485 | 3/1979 | Fed. Rep. of Germany . |
| 52-75569 | 6/1977 | Japan . |

OTHER PUBLICATIONS

Abstract–Japanese patent JA094426, 2-80.
Technical Bulletin: Altosid ® Briquet Product Applications Bulletin, Zeocon Corp., Palo Alto, Calif.
King, Chem. Abst. vol. 71 (1969) 104980b.
Bulletin No. TAC-150, "Plaster Mixing Procedures", United States Gypsum, Chicago, Ill.

*Primary Examiner*—Catherine L. Mills
*Attorney, Agent, or Firm*—Merchant, Gould, Smith, Edell, Welter & Schmidt

[57] ABSTRACT

A controlled slow release pest control composition comprising an encapsulated pesticide, carbon and plaster.

23 Claims, No Drawings

TIMED RELEASE PEST CONTROL COMPOSITION AND MEANS

This is a continuation of application Ser. No. 472,922, filed Mar. 7, 1983, abandoned.

FIELD OF THE INVENTION

The invention relates to a pest control composition and a means for pest control which can be distributed throughout the environment to slowly release an effective pest controlling amount of a pesticide and to control pest population throughout the temperate months.

BACKGROUND OF THE INVENTION

During the temperate months of the year, the population of many pests in portions of the United States reaches levels which causes severe problems. One pest, the mosquito, can be distracting, can cause bites which itch and in certain cases can be a vector for the spread of communicable disease. Mosquito populations vary during the temperate periods of the year depending on rainfall, temperature, and other conditions. While the life span of an adult mosquito is not long, mosquito larvae can continually mature throughout the year into the adult stage, resulting in the continuing resupply of the mosquito population. Many communities have combatted mosquito populations by fogging or spraying the environment with insecticide, adding insecticide to likely hatching sites, and by distributing a variety of slow release insecticide compositions into the environment.

Many other pests can cause severe problems during the fair months of the year. Mollusks in both the adult and larval forms can infest fresh water, can damage flora and fauna, can be a disease vector, and can pose cosmetic problems. Fungi and algae can grow rapidly in fresh water and make water unpleasant for recreational purposes, can produce toxins which can poison farm animals and make water unfit for human consumption. A variety of plants can grow in unwanted areas reducing crop yields and presenting weed control problems in many residential and agricultural environments. Many attempts have been made to combat these pest problems using a variety of pesticides.

Pesticides have been encapsulated with both macro and microencapsulation processes in ceramic materials, biodegradable polymers, porous mineral supports, cellulose derivatives, polyurea compounds, gypsum and other supports in order to protect the insecticide from the environment and to insure a controlled release attempting substantial control of pest populations. I have had substantial experience with a number of these pesticide compositions and have found that they fail to provide one or more of the following properties. The pesticide must be released at a rate such that its concentration in the environment is maintained at at least an effective pest control concentration throughout the temperate part of the year in order to control pest populations at the time they appear. The pesticide should be released at an even rate such that significant amounts are not wasted. Pesticides should be protected from the effects of atmospheric oxidation, electromagnetic radiation (light energy or UV radiation) or other factors, which can cause the photochemical decomposition of the pesticide.

Accordingly a substantial need exists for a controlled slow release insecticide composition that can provide substantial control of pest populations throughout the temperate season, can provide a controlled continuous rate of release that maintains an effective mosquito controlling concentration of the insecticide in the environment, and which protects the insecticide from substantial degradation.

BRIEF DISCUSSION OF THE INVENTION

I have found that a composition comprising a pesticide, preferably in a slow release encapsulated form, a specified high compressive strength plaster, also called gypsum cement, and finely divided carbon particles can provide efficient control of pest populations throughout the temperate season while protecting the pesticide from the harmful effects of electromagnetic radiation. The novel slow release insect control composition can be distributed in the environment in a variety of forms, spheres, cylinders, polygons, blocks, etc. For reasons of ease of manufacture and controlled decomposition, it is most commonly distributed in the environment in the form of a cylinder or truncated cone (a tapered cylinder) which slowly decomposes throughout the temperate season until it is substantially gone. The encapsulated slow release insecticide in combination with plaster or gypsum cement provides a continual smooth release of the insecticide at a constant rate resulting in the constant effective pest controlling concentration of the insecticide in the environment without releasing intermittantly excessive amounts of pest control agent. The plaster tends to dissolve at a near steady rate in the presence of environmental water, releasing encapsulated insecticide into the environment. The decomposition is most effective when the pest control means is fully immersed in water. The carbon in combination with the insecticide both protects unreleased insecticide from the harmful effects of the electromagnetic radiation and at the same time acts as a secndary release mechanism as the absorbed concentrated pesticide rereleases slowly from the carbon particle, resulting in a more constant rate of release of the insecticide. The nature of the carbon particles is such that they can absorb substantial quantities of the impinging ultraviolet light before it can penetrate the pest control means degrading the pesticide. Further, carbon particles have a large surface area which can absorb the excess insecticide as it is released, smoothing the release of the insecticide into the environment. Accordingly, each of the components of the composition cooperates with the other components, protecting insecticide from the harmful effects of electromagnetic radiation and providing insect control during the entire pest season. It should be clearly understood that by the term pest, I mean any living organism, plant, animal or microbe, whose presence causes human discomfort, harm to agriculture, a health hazard, or cosmetic harm. The term pesticide means any chemical agent effective in pest control, that operates to control pest populations which prevents maturation or reproduction, or which kills the pest with toxic effects.

DETAILED DISCUSSION OF THE INVENTION

Briefly, the controlled slow release pesticide composition comprises an encapsulated pesticide, a specific high strength plaster or gypsum cement composition, and finely divided carbon particles. The pest control means made of the controlled slow release pesticide composition must have a specific surface area to provide an effective concentration pest control agent.

PESTICIDE

The term pesticide as employed here is intended to include any active material used for control of unwanted plants, animals, or microorganisms, such as mosquitos, fungi, algae, snails, weeds, including in particular insecticides, biocides, and other materials utilizable in the environment.

A great variety of insecticides can be used which are compatible with the plaster and carbon particle components of the invention. Representative of the pesticides which may be employed as starting materials in the invention are disclosed in U.S. Pat. No. 4,225,693, which are expressly incorporated by reference herein, in order to provide examples of insecticide compositions, which include, in general, the following classes. Triazole insecticides, arsenic based insecticides, sulfonyl carbamate insecticides, thiazine insecticides, benzonitrile insecticides, which are set forth in column 3, lines 21-70, column 4, 5, and 6, lines 1-10. No list of useful insecticides can be complete since there are insecticides fo which I am not aware and new insecticides which will be developed in the future. However, any insecticide having insect control properties which can be compatible with plaster and carbon can be used in the invention.

The pesticides which are preferred for use in the invention are trichloroacetic acid, 2,4-dichlorophenoxyacetic acid and 2,4-DW, a relatively new pesticide 4-amino-6-tertiary butyl-3-(methylthio)-AS-triazine-5(4HN)-one, which is available under the name Metabucin. The most preferred mosquito insecticide comprises isopropyl-(2E,4E)-11-methoxy-3,7,11-trimethyl-2,4-dodecadienoate, which is the active ingredient in the composition, available under the trade name Altosid SR-I0 from Zoëcon Corp. Altosid SR-10 is an insect specific growth regulator that acts to prevent the emergence of adult mosquitoes from the pupae stage by affecting the maturation process and is not a nondiscriminant toxin.

Many fungi can be controlled using the pest control means of this invention in a variety of environments, including agricultural and industrial applications. In agricultural applications fungi can often harm the maturation of agricultural plants or animals, resulting in the loss of valuable commodities. In industrial applications, fungi often grow in places where water accumulates such as cooling towers, streams, tanks, filtration mechanisms, etc., causing plugging, odor problems, etc. Fungal control agents which can be used in the pest control means of the invention include sulfur, polysulfides, heavy metal fungicides, such as copper based, arsenic based, and mercury based fungicides, including for example copper hydroxide, copper carbonate, cuprous oxide, O-(chloromercury)phenol, cresylmercuric cyanide, methylmercuric-8-hydroxy quinolate, phenyl mercuric acetate, and phenyl N-(ethylmercury)-paratoluene sulfonamide; organic fungicides such as quinones, such as chlorinel, dichlone, and others. Organic sulfur based fungicides include ferric dimethyl dithiocarbamate, zinc dimethyl dithiocarbamate, and sodium methyl dithiocarbamate; and other classes of organic fungicides including imidazoline based fungicides, quinoline based fungicides, trichloromethyl thiodicarboxamide based fungicides, and others.

Molluscacides can be incorporated into the pest control composition of the invention. Mollusks are invertebrates which comprise snails, slugs, oysters, mussles, cuttle fish, squid, and other animals. Mollusks can attack crops, flower gardens, and infest fresh water and can be the vector for a variety of disease causing parasites. Molluscacides useful in the invention include metaldehyde, antimony based molluscacides, carbamate based molluscacides such as isolayn or sectraon. Molluscacides that can be used include copper sulfate, copper dimethyl dithiocarbamate, dinitrol phenol based molluscacides such as 2,4-dinitro creosol and any other molluscacide that can be incorporated without adverse effect into the composition of the invention.

Herbicides that can be used to effectively control unwanted plants in residential or agricultural environments are well known chemical herbicides that kill growing plants or prevent seed germination of plant growth. Most useful herbicides belong to compound classes including the phenoxy alkanoic acid such as 2,4-D, 2,4,5-T, 2,4-DD, MCPA; the S-triazines, cymazines, detrazine, propyzene; the phenyl carbamates, IPC, CIPC, barban; the chlorinated aliphatic acids, delapon, TCA; the phenylureas (fenuron, monuron, diuron); the dinitrobenzenes (DNBP, trifluoralin, benefin); the benzoic acids, amiben, 2,3,6-TBA; the dipyridyls (paraquot, diquot); and the dithiocarbamates, EPTC, and vernolate.

Algecides can also be incorporated into the slow release pest control means of the invention. A variety of both organic and aeroganic algecides are well known in the art.

PLASTER

Dehydration of gypsum (calcium sulfate dihydrate, $CaSO_4 \cdot 2H_2O$) in an open kettle by direct heating in the range of 390°-570° F. will result in beta-calcium sulfate bemihydrate, $CaSO_4 \cdot O.5H_2O$, commonly called plaster. Typically the plaster crystals are long, needle-like, irregular in shape and porous. The shape and porosity of the crystalline particles results in high water absorbency. The powder, when mixed with water, will require about 60 parts of water to about 100 parts of plaster to give a "workable" consistency. Plasters can contain a variety of additives which provide properties such as wettability, strength, hardening rate, particle size, and low viscosity slurries.

Preferred plaster compositions having a controlled rate of disintegration or deterioration in the environment comprise plasters can slowly disintegrate over a time period of 120 to 180 days and can expose the pesticides into the environment during the decomposition period.

The most preferred plaster for making the improved slow release mosquito control compositions of this invention comprise a high density, high compressive strength plaster having a density of at least 1,600 grams per liter and compressive strength of at least 5,000 lbs. per square inch, preferably 9,000 lbs. per square inch, more preferably about 10,000-15,000 lbs. per square inch and greater, for reasons of its slow decomposition in the environment, resulting in the extended lifetime of the composition in the environment and a mosquito controlling concentration of the pest controlling agent throughout the temperature season.

While we do not wish to be held to a theory of action of the pest control means of this application, we believe that the high density, high compressive strength of the plaster is a result of the crystal structure of the calcium sulfate hydrate that makes up the plaster. The crystal structure of high compressive strength plaster results in a controlled steady rate of solubility which in turn controls the release of the pesticide. The crystals in the plaster appear to overlap and interact, resulting in a high density plaster having increased compressive strength and a controlled rate of solubility resulting from the crystal structure. These properties appear to be essential in providing the controlled solubility and controlled release of the pesticide compositions.

CARBON

Finely divided carbon compositions useful in the invention for making the delayed release mosquito control composition of the invention are carbon compositions having large surface area and small particle size, providing the electromagnetic radiation protection and the release smoothing properties. As the pest control means comprising the slow release composition decomposes, the mosquito controlling agent is released. The carbon in the composition tends to smooth the release rate by absorbing extra concentrations of insecticide when the release rate is high and by releasing or desorbing the insecticide when the release rate is low. The carbon particles in combination with the encapsulated or micro-encapsulated pesticide also appear to control the release locus of the pesticide. Objects with a specific gravity substantially less than 1.0 tend to float while those with a greater specific gravity tend to sink. Many pesticide compositions have a specific gravity substantially less than 1.0 which results in the pesticide floating to the surface where it can be rapidly degraded by contact with light and air. The micro-encapsulated pesticides in combination with carbon can have a specific gravity greater than 1 which results in the carbon-pesticide combination maintaining a constant depth or sinking to the bottom where it can be released. By adjusting the specific gravity of the plaster carbon pesticide combination the speed with which the pesticide reaches the surface of the body of water can be closely controlled. The carbon particles also protect the insecticide by absorbing electromagnetic radiation commonly in the form of ultraviolet radiation and preventing the deterioration of the insecticide through the effects of such radiation.

Accordingly, preferred particulate carbon useful in the invention has large surface area and small particle size found in carbon sources such as activated carbon, finely divided charcoal, etc. further details of sources of finely divided carbon is found in Kirk-Othmer Encyclopedia of Chemical Technology, Second Edition, Volume IV, pages 149–335.

In somewhat greater detail, the slow release pest control composition is formed from an effective amount of a slow release mosquito control compound, sufficient plaster to result in a slow dissolution of plaster lasting throughout the temperate season, commonly 140 days, sufficient amount of charcoal to prevent decomposition of the insecticide, and to smooth the release of the insecticide and sufficient water to be workable in manufacture and to cause the mixture to form a solid object which can be distributed throughout the environment.

The slow release pest control composition can take the form of a pest control means having essentially any regular or irregular three-dimensional shape including spheres, oblate spheres; polygons such as cubes, dodecahedrons, pyramids; cylinders, pyramids, cones, truncated cones; pillows, briquettes, etc. The release rate of the pest control agent from the means appears to be proportional to the means' surface area. The surface area should range from about 500 to about 50,000 $mm^2$, preferably about 1,500 to 25,000 $mm^2$ and most preferably about 2,500 to 7,500 $mm^2$ depending on the concentration of the pesticide to the means for reasons of economy and ease of handling. The preferred form of the slow release composition is in the form of a cylinder having dimensions of about 10 to 100 millimeters in diameter, and 10 to 100 millimeters in depth.

The most preferred form of the slow release composition is in the form of a truncated cone. I have discovered that in methods for manufacturing the slow release pest control object that in most processes for molding the objects the most difficult step is unmolding the objects from a form. I have found that the form which leaves the mold intact with minimum breakage has the form of a truncated cone wherein the minor radius is formed at the bottom of the mold and the major radius is formed at the top. I have found that for reasons of ease of molding and balanced release of the slow release compositions, the major diameter of the truncated cone should be about 20 to 45 millimeters, that the minor diameter of the truncated cone should be diameter of about 15 to 35 millimeters, and that the cone should be from about 15 to 40 millimeters in depth. Commonly the cone should have about 6 to 120 grams of material.

The most preferred embodiment of the pest control means for use with mosquito control comprises a truncated cone, including Altosid SR-10, having a major diameter of about 35 to 40 millimeters, a minor diameter of about 30 to 35 millimeters, a height of about 30 to 35 millimeters, a mass of about 35 to 45 grams and a total surface area of about 4,000 to 7,000 $mm^2$.

The composition can also be formed into objects having a substantial irregular shape, however sufficient amount of the composition should be included in the object so that substantial pest control concentrations of the insecticide composition is present in the environment through the substantial portion of the insect season.

The slow release pest control composition can comprise from about 15 to 80%, preferably about 20 to 75% and most preferably about 35 to 55% plaster, depending on the length of the temperate season. The slow release composition can comprise 80 wt-% or less of an encapsulated pest control agent, preferably 70% or less of the encapsualted pest control agent, and most preferably, for reasons of economy, ease of handling and effective pest control the composition can contain about 1 to 25 wt-%, preferably 2 to 15 wt-%, most preferably for reasons of efficient mosquito control throughout the temperate season about 3 to 8 wt-% of the pest control agent. Alternatively the amount of pesticide including encapsulating material will be less than about 50 wt-%, preferably about 1 to 25 wt-%, most preferably about 3 to 16 wt-%. The composition can comprise less than about 10 wt-%, preferably less than about 8 wt-%, most preferably about 4 to 6 wt-% of charcoal or activated carbon in order to protect the insecticide and to control the release of the insecticide composition. Sufficient water is added to the mixture of dry components sufficient to hydrate the plaster to bind the components together so that the composition can be formed into objects which can be distributed in the environment. Commonly an amount of water in the range of 25 to 50 wt-% of the composition can be present in the wet mix before molding. The water can be derived from the pesticide compound or can be added separately.

Depending on the insect season, control of insect populations can be maintained over varying time frames, depending on the surface area and composition of the object distributed in the environment. Protection can be maintaied for as little as 5 to 30 days and for as long as 150 days. An object having from 10 to 20 grams of material can provide pest control for 30 to 80 days. A pest control means object having from about 25 to 40 grams can provide a controlling amount of pest control agent for 80 to 150 days.

In general we have found that the pest control means can be applied to a site at a rate of about 150 to 350 means per acre, preferably 170 to 220 means per acre, most preferably about 180 to 200 means per acre. Commonly the spacing of pest control means at the breeding site can be about 10 to 30 feet between briquettes, preferably 15 to 25 feet, most preferably about 14 to 20 feet. The even distribution of the briquette can be important in controlling mosquitoes through likely breeding territories where the topography is substantially unknown. In certain areas where the topography is more familiar such a uniform distribution scheme is not absolutely necessary. In large areas of known topography where substantial water accumulates, we have found that it is important to introduce sufficient pest control means to provide a pest controlling amount of pesticide to the water and the pest control means do not have to be uniformly distributed. It is important that sufficient pest control means are positioned at the deepest spot in the area which is to be treated so that during the presence of any standing water the pest control means is exposed to the action of the water releasing pesticide. The balance of the pest control means can be distributed almost in any fashion through the area. Keeping in mind that at least some pest control means should be placed at a location such that as the area become simmersed in water sufficient pest control means are present to release pest controlling amounts of pesticide into the water.

The pest control means can be distributed into the environment by hand, can be distributed from ground vehicles or boats, can be distributed by helicopter or other aircraft, or any other means insuring a fairly even distribution of the pest control means into the environment. The pest control means of the invention can be distributed into any environmental location which is seasonally flooded or contains standing water during a substantial portion of the season. Typical wetland areas which can be treated using the pest control means of the invention are seasonally flooded basin or flat sites typical of woodland areas having few aquatic plants or grasses. Such sits generally are flooded during the wetter periods of the temperate season. Inland fresh meadow areas contain standing water for greater periods of time during the year and are commonly characterized by the presence of reeds, canary grass or other plants common in a wetter environment. Inland shallow fresh water marshes are commonly muddly throughout the growing season with about 6 inches of water, commonly characterized by the presence of cattail ranks, and grass across geographically depressed areas. Inland deep water, fresh water marshes commonly have water year- around, pockets of open water permitting submerged aquatic plants to grow, and can have as much as six inches to three feet of water permanently present. Inland open fresh water such as game lakes commonly have fresh water present at depths of greater than 10 feet, and can be characterized by depths free of vegetation while vegetation is commonly present in the shallows or at the water edge. The pest control means can be used in any of these wetland areas in order to control pest populations. Mosquitoes, for example, are most commonly produced in areas that area seasonally flooded or where the water depth fluctuates.

The pest control means can be applied to an environment that is substantially dry or wet. In a dry environment (no standing water) atmospheric humidity will result in little pesticide release. In wet environments (standing water) where the pest control means is immersed, water that induces decomposition will generally be environmental standing water. It is to be understood that decomposition is generally favored and is most efficient in the presence of standing water.

EXAMPLE I

Into a 15 gallon steel tank was placed 5 gallons of a slurry of micro particulate encapsulated mosquito control agent isopropyl-(2E,4E)-11-methoxy-3,7,11-trimethyl-2,4-dodecadenoate (Altosid SR-10 5–10 micron particles, 10% slurry of micro encapsulated particles in water, 10.86 lb./gal. (103 gm/L) active). The slurry was mixed with a mortar mix paddle attached to a hand held drill driven at 800 rpm until the slurry was uniform. Into the uniform slurry was added 4 lbs. Norit SG charcoal powder and the mixture was again agitated until uniform. Into the mixture was placed 62 lbs. of plaster (DieKeen [Rockeen] dental plaster, compressive strength 13,500 psi), 3.3 quarts of distilled water and 500 grams of plaster set accelerator (Terra Alba). The mixture was agitated with the mortar mix paddle for eight minutes until fully mixed. The mixture became creamy at four minutes indicating that the plaster was fully wetted.

The pest control mixture was poured onto an RTV rubber mold having 1100 individual molds each in the form of a truncated cone having approximate dimensions of 37 millimeters in major diameter, 33 millimeters in minor diameter, and 31 millimeters in height. Each of the molds accepted 40 grams of plaster material. After the plaster mixture was added to the molds, the plaster mixture was distributed throughout the mold sheet with a spatula, the mold was tapped to release trapped air, and the excess plaster was removed from the top of the mold with the float which also evened the material. The plaster objects hardened within about one and one half hours and were popped from the rubber mold into a trough, and were then ready for bagging. The compressive strength of the objects ranged from 220–350 psi.

TABLE I

Summary of field trial with mosquito control means in which water remained through adult emergence enabling the determination of cumulative mortality. Tests were conducted on floodwater *Aedes* species April through September.

| Dosage Rate/ft$^2$ | Number of Tests | Cumulative Percent Mortality in Each Test | Mean Percent Mortality |
|---|---|---|---|
| 1/64 | 1 | 100 | 100 |
| 1/100 | 2 | 100, 100 | 100 |
| 1/144 | 2 | 100, 100 | 100 |
| 1/156 | 4 | 100, 100, 100, 100 | 100 |
| 1/225 | 6 | 95, 100, 100, 100, 100, 99 | 100[1] |
| 1/256 | 3 | 98, 100, 98 | 99 |
| 1/289 | 1 | 100 | 100 |
| 1/306 | 6 | 84, 100, 96, 100, 97, 82 | 94 |
| 1/324 | 1 | 100 | 100 |

TABLE I-continued

Summary of field trial with mosquito control means in which water remained through adult emergence enabling the determination of cumulative mortality. Tests were conducted on floodwater *Aedes* species April through September.

| Dosage Rate/ft$^2$ | Number of Tests | Cumulative Percent Mortality in Each Test | Mean Percent Mortality |
|---|---|---|---|
| 1/400 | 1 | 78 | 78 |

[1]In the first test which achieved 95 percent control the water was polluted from manure pile runoff, not a normal site. Dropped test when computing the mean percent mortality.

TABLE II

Detailed results of field trials with mosquito control means in which water remained through adult emergence enabling the determination of cumulative mortality. Tests were conducted on floodwater *Aedes* species April through September.

| Dosage rate/ ft$^2$ | Date Treated | Flood No. | 1st | 2nd | 3rd | 4th | Pupae | Adult | Cumlt. |
|---|---|---|---|---|---|---|---|---|---|
| 1/64 | 4/23 | 1 | | | | Site dried up | | | |
| | | 2 | | | | 1 | 99 | | 100 |
| 1/100 | 4/23 | 1 | | | | | 100 | | 100 |
| | 4/23 | 1 | | | | 68 | 32 | | 100 |
| 1/144 | 4/23 | 1 | | | | 26 | 72 | 2 | 100 |
| | 4/23 | 1 | | | | 45 | 49 | 6 | 100 |
| 1/156 | 6/6 | 1 | 100 | | | | | | 100 |
| | 6/6 | 1 | | | 65 | | 35 | | 100 |
| | 6/10 | 1 | | | | 25 | 75 | | 100 |
| | 6/10 | 1 | | | | 2 | 98 | | 100 |
| 1/225 | 5/20 | 1 | | | | 2 | 89 | 4 | 95 |
| | 5/20 | 1 | 100 | | | | | | 100 |
| | | 2 | | | | Site dried up | | | |
| | | 3 | 100 | | | | | | 100 |
| | | 4 | | | | 7 | 2 | 39 | 41 |
| | 6/5 | 1 | 100 | | | | | | 100 |
| | 6/6 | 1 | | | | 2 | 92 | 6 | 100 |
| | 6/7 | 1 | | | | 6 | 94 | | 100 |
| | 6/26 | 1 | | | | 28 | 68 | 3 | 99 |
| 1/256 | 6/27 | 1 | | | | No data | | | |
| | | 2 | | | Site dried with delayed development | | | | |
| | | 3 | | | | | 86 | 12 | 98 |
| | 7/29 | 1 | | | | 59 | 41 | | 100 |
| | | 2 | | | | 30 | 55 | 15 | 100 |
| | 8/8 | 1 | | | | 4 | 88 | 6 | 98 |
| 1/289 | 8/21 | 1 | | | | 100 | | | 100 |
| 1/306 | 6/2 | 1 | | | | 3 | 51 | 30 | 84 |
| | | 2 | | | Site dried with delayed development | | | | |
| | | 3 | | | | 7 | 24 | 14 | 45 |
| | 6/6 | 1 | | | | | 100 | | 100 |
| | 6/6 | 1 | | | | 39 | 49 | 8 | 96 |
| | | 2 | | | | 95 | 3 | 2 | 100 |
| | | 3 | | | Site dried with delayed development | | | | |

An examination of Tables I and II clearly shows the effectiveness of the pest control means in obtaining 100% mortality in Aedes mosquito species during the temperate season. It is clear that at a rate of 1 pest control means per 225 to 256 square feet or greater dosage rate results in essentially 100% mortality of adult mosquitoes. It appears that at lesser dosage rates confidence in 100% mortality kills is reduced. Further, the mortality of the fourth Instar stage and pupae stage appear to be the primary killing mechanism for mosquitoes indicating the active ingredient in the pest control means indeed results in the death of the mosquito populations. Again, it is clear that at dosage rates of 1 pest control means per 225 to 456 square feet, essentially 100% mosquito kills can be expected.

The above discussion and Examples provides a basis for understanding and practicing the invention. However, since many embodiments of the invention can be made without departing from the spirit and scope of the invention, the invention resides solely in the claims hereinafter appended.

I claim:

1. A controlled slow release pest control composition that can be hardened by the addition of a sufficient plaster hydrating amount of water, which consists essentially of an effective pest population controlling amount of a pest control agent, a plaster having high compressive strength of at least about 5,000 lbs. per square inch, and an effective electromagnetic radiation absorbing amount of finely divided carbon wherein the composition can be used in the form of a solid pest control means that when immersed in an aqueous pest breeding site can release an effective amount of the pest control agent for at least 30 days, and that when dry does not release the agent.

2. The composition of claim 1 wherein the pest control agent comprises an insecticide, a herbicide, an algicide, a molluscacide, or a fungicide.

3. The composition of claim 1 wherein the pest control agent is encapsulated.

4. The composition of claim 3 wherein the encapsulated pest control agent comprises an insecticide which is present in the total composition at an amount of about 50 wt-% or less.

5. The composition of claim 4 wherein the insecticide is a mosquito control agent.

6. The composition of claim 5 wherein the mosquito control agent comprises isopropyl-(2E,4E)-11-methoxy-2,7,11-trimethyl-2,4-dodecadiene.

7. The composition of claim 1 wherein the compressive strength of the high compressive strength plaster ranges from about 9,000 to about 15,000 pounds per square inch.

8. The composition of claim 7 wherein the compressive strength of the high compressive strength plaster ranges from about 10,000 to 14,000 pounds per square inch.

9. The composition of claim 1 wherein the pest control agent is present in the total composition in an amount of about 3 to about 16 wt-%.

10. The composition of claim 1 wherein the plaster is present in the total composition in an amount of about 30 to 90 wt-%.

11. The composition of claim 1 wherein the finely divided carbon is present in the total composition in an amount of about 1 to about 15 wt-%.

12. A solid pest control means which consists essentially of an effective amount of a pest control agent, an effective slow release amount of a plaster having a high compressive strength of at least 5,000 lbs. per square inch, an effective ultraviolet light absorbing amount of finely divided carbon particles, and a plaster hardening amount of water, wherein the object is hard, can be distributed over large areas by mechanical means, has a surface area of about 500 to about 50,000 mm$^2$, when immersed in an aqueous pest breeding site can provide an effective amount of the pest control agent for at least 30 days, and when dry does not release the agent.

13. The solid pest control means of claim 12 wherein the surface area of the object is about 2,500 to 25,000 mm$^2$.

14. The solid pest control means of claim 13 wherein the surface area of the object is about 2,500 to 7,500 mm$^2$.

15. The pest control means of claim 12 wherein the solid pest control means has a regular shape.

16. The pest control means of claim 15 wherein the regular shape is a briquette, a pillow, a sphere, a prism, or a pyramid.

17. A pest control means of claim 15 wherein the regular shape is a cylinder having dimensions of about 10 to 100 millimeters in diameter and about 10 to 100 millimeters in height.

18. The pest control means of claim 15 wherein the regular shape is a truncated cone having dimensions of about 20 to 45 millimeters on the major diameter, about 15 to 35 millimeters on the minor diameter, and about 15 to 40 millimeters in height.

19. The pest control means of claim 17 wherein the dimensions of the truncated cone are about 35 to 40 millimeters in the major diameter, about 30 to 35 millimeters in the minor diameter, and about 30 to 35 millimeters in height.

20. The solid pest control means of claim 19 wherein the surface area of the solid pest control means is about 4,000 to 7,000 mm$^2$ and wherein the mass of the solid pest control means is about 35 to 45 grams.

21. A method of controlling pest populations which comprises distributing the solid pest control means of claim 12 into an aqueous environment.

22. The method of claim 21 wherein the solid pest control means are applied uniformly in the environment at a rate of about 150 to about 250 pest control means per acre.

23. The method of claim 21 wherein the pest control means are distributed in the environment such that they are about 10 to 30 feet apart.

* * * * *